United States Patent [19]

Suzuki et al.

[11] Patent Number: 5,079,595
[45] Date of Patent: Jan. 7, 1992

[54] ORGANIC THIN FILM SEMICONDUCTOR DEVICE

[75] Inventors: Shoji Suzuki; Hideo Saeki, both of Hyogo, Japan

[73] Assignee: Mitsubishi Denki Kabushiki Kaisha, Tokyo, Japan

[21] Appl. No.: 428,552

[22] Filed: Oct. 30, 1989

[30] Foreign Application Priority Data

Nov. 2, 1988 [JP] Japan .................. 63-277732

[51] Int. Cl.$^5$ ............ H01L 29/28; H01L 29/66; B05D 1/18
[52] U.S. Cl. ........................ 357/8; 357/25; 427/430.1; 427/435
[58] Field of Search ........ 437/1, 225; 357/25, 357/8; 350/357

[56] References Cited

U.S. PATENT DOCUMENTS

| | | | |
|---|---|---|---|
| 4,571,029 | 2/1986 | Skotheim et al. | 350/357 |
| 4,586,980 | 5/1986 | Hirai et al. | 427/264 |
| 4,721,601 | 1/1988 | Wrighton et al. | 357/25 |
| 4,745,327 | 5/1988 | Saeki et al. | 313/371 |
| 4,807,977 | 2/1989 | Sammells | 350/357 |
| 4,816,290 | 3/1989 | Heki et al. | 427/435 |
| 4,849,330 | 7/1989 | Humphries et al. | 357/25 |
| 4,972,370 | 11/1990 | Morimoto et al. | 357/8 |
| 4,987,430 | 1/1991 | Clarisse et al. | 357/8 |

FOREIGN PATENT DOCUMENTS

58-141246 8/1983 Japan .
62-170843 7/1987 Japan .

OTHER PUBLICATIONS

"Electronic Devices Incorporating Stable Phthalocyanine Langmuir-Blodgett Films", Roberts et al., *Thin Solid Film*, vol. 132, 1985, pp. 113-123.

Barger et al., "Derivatives of Phthalocyanine Prepared for Deposition as Thin Films by the Lanmuir-Blodgett Techniques", *Thin Solid Films*, vol. 133, pp. 197-206, (1985).

Kakimoto et al., "Heat Resisting LB Film", The Chemical Society of Japan, pp. 140-141, (1987).

*Primary Examiner*—Rolf Hille
*Assistant Examiner*—Mahshid Saadat
*Attorney, Agent, or Firm*—Lowe, Price, LeBlanc & Becker

[57] ABSTRACT

A method for manufacturing an organic semiconductor thin film (24) having an improved characteristic as a semiconductor is provided. A phthalocyanine compound having amino groups is mixed with stearic acid to form a bonded substance capable of being dissolved in an organic solvent. Then, an organic solution is made by dissolving this bonded substance in the organic solvent. By developing this organic solution on a water (20) surface, the thin layer (23) of this bonded substance is formed on the water (20) surface. Thereafter, this thin layer is moved onto a substrate (30) and accumulated to be deposited on the substrate (30). Next, the stearic acid is volatilized and removed from the above described thin film (23) deposited on the substrate (30) by baking the whole substrate. The thus structured organic semiconductor thin film (24) is used as a semiconductor material such as a photoelectric transfer device, a gas sensor, a transistor and the like.

7 Claims, 11 Drawing Sheets

M = Cu, Ni, Co, Fe etc.
Pb, Zn, Mg $X = -C(CH_2)_3$

M = Cu, Co, Ni, Fe, Pb
Zn, Mg etc.

X = $-NH_2$
= $-CO_2H$
= $-CONHC_nH_{2n+1}$
= $-NHCOC_nH_{2n+1}$
= $-COOC_nH_{2n+1}$

ORGANIC THIN FILM SEMICONDUCTOR DEVICE

BACKGROUND OF THE INVENTION

1. Field of the Invention

The present invention relates to a method for manufacturing an organic semiconductor thin film and a semiconductor device comprising the thin film- and, more particularly, to a method for manufacturing an organic semiconductor thin film having an improved characteristic as a semiconductor and a semiconductor device comprising the thin film.

2. Description of the Background Art

A Langmuir-Blodgett's technique (hereinafter referred to as a LB method) has been conventionally well known as a method for forming an organic semiconductor thin film. The Langmuir-Blodgett's technique will be briefly described in the following. FIGS. 1A to 1C show processes for accumulating thin films on a substrate by the Langmuir-Blodgett's technique.

Referring to FIG. 1A, an appropriate liquid such as water 20 is contained in a container. Thereafter, a material of a monomolecular film 23 is dissolved by an organic solvent to provide an organic solution. The organic solution is dropped in the water 20. The organic solution is spread over the surface of the water 20. Thereafter, the organic solvent is volatilized, leaving a monomolecular film 23 on the surface of the water 20.

Referring to FIG. 1B, as the substrate 21 is gradually lowered, the monomolecular film 23 is attached to the substrate 21. Thereafter, when the substrate 21 is left from the water 20, a substrate 21 having the monomolecular film 23 attached thereon is provided. By repeating the same operation, a substrate 21 having several to several ten layers of monomolecular films 23 accumulated thereon is provided, as shown in FIG. 1C.

For example, Japanese Patent Laying-Open No. 141246/1983 discloses technique of forming a phthalocyanine organic semiconductor thin film by the LB method from a tetra-tert-butyl phthalocyanine compound having four tert-butyl groups introduced in a molecule as shown in FIG. 2. In addition, another technique of composing the organic semiconductor phthalocyanine thin film by the LB method from the phthalocyanine compound having substituent groups (—CH$_2$NHC$_3$H$_7$) introduced in non-symmetrical positions in the molecule, as shown in FIG. 3 is disclosed in the literature (Thin Solid Films, 132, 113 (1985).

The above described substituent group is introduced to make phthalocyanine compound soluble in the organic solvent. The phthalocyanine compound is insoluble in the organic solvent unless such substituent group exists.

However, referring to FIG. 4A, t-butyl group has a large volume 25 occupying the space, since the t-butyl group comprises three methyl groups coupled to a tertiary carbon atom. That is the reason why t-butyl group is bulky.

When such a Pc compound having bulky substituent group is used for forming an organic semiconductor thin film in accordance with the above described LB method, the stacking of the cumulative layers is not sufficient as shown in FIG. 5A, so that t-butyl group 27 serves as an insulating layer, preventing effective use of the characteristic of the semiconductor.

In case of the phthalocyanine compound shown in FIG. 3, the substituent group (—CH$_2$NHC$_3$H$_7$) is introduced at non-symmetrical positions of the molecule. When an organic semiconductor thin film is formed by using such phthalocyanine compound in accordance with the LB method, packing of the cumulative layer is not sufficient. Consequently, the substituent group serves as an insulating layer, preventing effective use of the characteristics of the semiconductor.

SUMMARY OF THE INVENTION

An object of the present invention is to provide a method of manufacturing an organic semiconductor thin film improving characteristics of the organic semiconductor.

Another object of the present invention is to provide a semiconductor device formed by using organic semiconductor thin films whose characteristics as the organic semiconductor are improved In order to attain the above described objects, in the method of manufacturing an organic semiconductor thin film in accordance with the present invention, an organic semiconductor compound having a first substituent group and a long chain hydrocarbon having a second substituent group which can be coupled to the first substituent group are prepared.

Thereafter, the organic semiconductor compound having the first substituent group and the long chain hydrocarbon having the second substituent group are coupled to each other so as to make the organic semiconductor compound soluble in on organic solvent.

Thereafter, the organic semiconductor compound coupled to the long chain hydrocarbon is dissolved in the organic solvent, thereby providing an organic solution. The organic solution is dripped to an appropriate liquid so as to make a layer of the organic solution on the liquid.

Thereafter, the solvent is removed and a layer of the combination of the organic semiconductor compound and a long chain hydrocarbon is formed on the liquid.

Thereafter, the layer of the combination of the organic semiconductor compound and the long chain hydrocarbon is deposited on a surface of a substrate. Then, the long chain hydrocarbon is removed from the combination in order to form an organic semiconductor film formed of the organic semiconductor compound having the first substituent group on the substrate.

The semiconductor device in accordance with another aspect of the present invention is formed by employing the organic semiconductor thin film formed through the above described steps as the semiconductor layer.

According to the method of manufacturing the organic semiconductor thin film of the present invention, a layer of a combination of an organic semiconductor compound having a first substituent group and a long chain hydrocarbon having a second substituent group is deposited on a surface of the substrate, and thereafter the long chain hydrocarbon having the second substituent group is removed from the resulting thin film. When amino group 28 or carboxyl group is used as the first substituent group, the thin film left on the substrate is formed only by an organic semiconductor compound having the substituent group (amino group 28, carboxyl group 29) which has very small volume occupying the space, as shown in FIGS. 4B and 4C. Referring to FIG. 5B, the amino group 28 is left, however, the amino group is not bulky, so that packing and stacking can be carried out with sufficient density of the moleculars. A semiconductor device having highly improved characteristics can be provided by utilizing the organic semiconductor thin film formed in this manner in the semiconductor device.

The foregoing and other objects, features, aspects and advantages of the present invention will become more apparent from the following detailed description of the present invention when taken in conjunction with the accompanying drawings

DESCRIPTION OF THE PREFERRED EMBODIMENTS

A description is made of embodiments of the present invention.

EXAMPLE 1

Figure 1A:
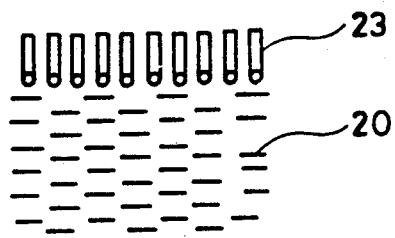
FIGS. 1A to 1C show processes of the Langmuir-Blodgett's technique.
Figure 1B:
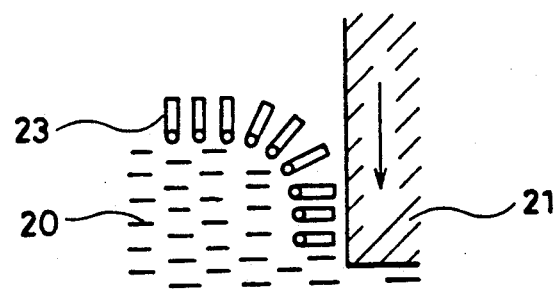
Figure 6:
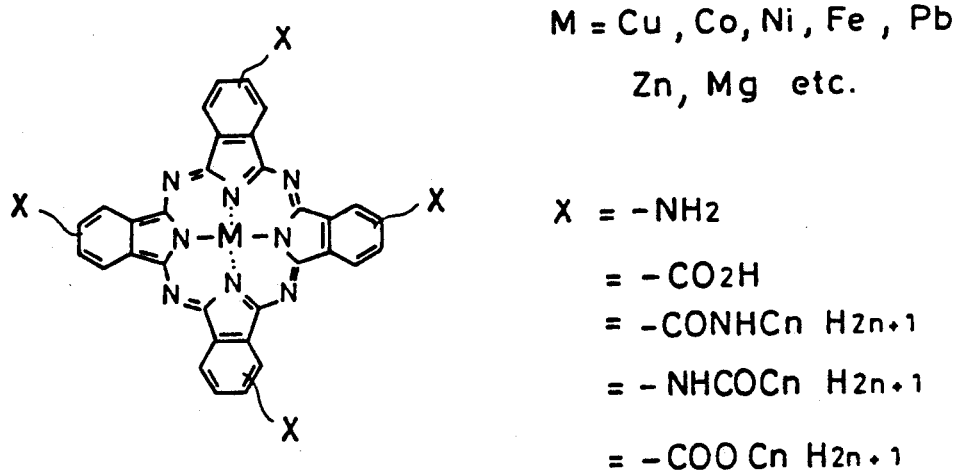
FIG. 6 shows a structural formula of a phthalocyanine compound used in the present invention.

Referring to FIG. 6, a phthalocyanine compound (hereinafter referred to as a Pc compound) having four amino groups of an essential minimum size introduced thereto was used as an organic semiconductor compound. Cu was selected as a center metal M. A phthalocyanine compound including an amino group and a stearic acid which is a fatty acid with long alkyl chain generally represented by $C_nH_{2n+1}COOH$ are mixed in a ratio of 1:4 to form a combination (hereinafter referred to as an amine salt). The amine salt is dissolved in an appropriate organic solvent such as chloroform, xylene, dimethylacetamid, N-methylpyrolidone such that the concentration of the Pc compound is between approximately $1.0 \times 10^{-4}$M. Resulting organic solution is dripped in water 20, as shown in FIG. 1A. The organic solution is spread over the surface of the water 20. Thereafter, the organic solvent is volatilized, leaving a monomolecular film 23 of the amine salt on the surface of the water 20. Referring to FIG. 1B, a substrate 21 such as a glass plate (when electrical characteristics are to be measured, electrodes may preferably be formed on the substrate 21) is lowered to be dipped in the water 20. The monomolecular film 23 of the amine salt is attached to the substrate 21. The lifting speed of the substrate 21 in the dipping method is 5 mm/min.

Figure 1C:
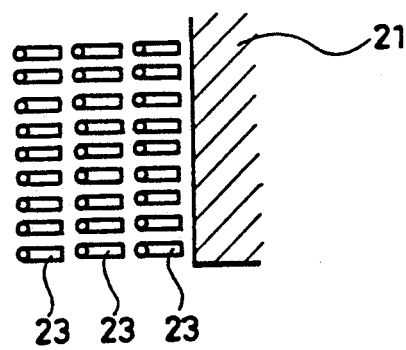
Figure 2:
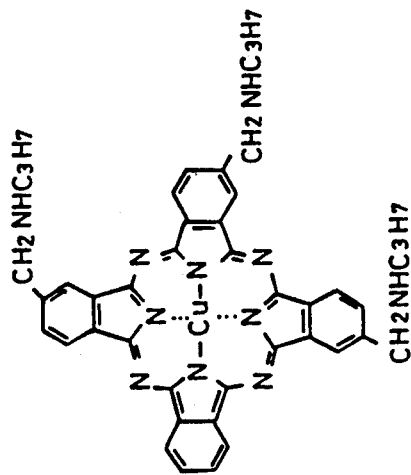
FIG. 2 shows structural formulas of a tetra-tert-butyl phthalocyanine compound.

By repeating the same operation, several to several ten layers of the monomolecular films 23 are accumulated on the substrate, as shown in FIG. 1C. Thereafter, the substrate is heated in $N_2$ for 1 to 2 hours at the temperature of the 300° to 320° C.

This heating treatment might be carried out for each layer The stearic acid was volatilized and removed during this heating treatment. This volatilization of the stearic acid was confirmed by comparing IR absorption spectra of a specimen before and after baking. More specifically, there was absorption (approximately $2800 \sim 3000$ cm$^{-1}$) due to C—H stretching vibration peculiar to an alkyl chain of the stearic acid in the specimen before baking, but this absorption was hardly recognized in the specimen after baking. An insulating side chain did not remain in the thus formed thin film. Therefore, this thin film had an excellent electric characteristic because of its high stacking characteristic.

The used Pc compound had a hydrophilic property portion formed extending in all directions of a Pc ring. Therefore, the bonded Pc compound and fatty acid with long alkyl chain had a structure in which a long chain alkyl group having a hydrophobic property existed near this portion having the hydrophilic property. As a result, when the organic solution of the bonded Pc compound and fatty acid with long alkyl chain was developed on the water surface, the long alkyl chain was directed to the side of a gaseous phase of a gas-liquid interface. In this case, the long chain alkyl chain was orientated about vertically to the water surface and the Pc ring plane was orientated parallel to the water surface. Consequently, the organic semiconductor thin film provided in this embodiment was much better than the thin film formed from a conventional Pc compound also as far as orientation is concerned. In addition, according to reports until now, the occupied area of the tetra-tert-butyl phthalocyanine and the like was $87 \sim 96$ Å$^2$, but the occupied area of the thin film formed by the above described method was as big as $150 \sim 180$ Å$^2$. This fact proved that the Pc ring was oriented parallel to the substrate surface.

The steps of forming the thin film in accordance with this example were as follows:

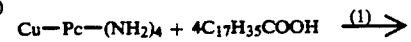

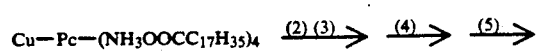

where (1) is the step of dissolving the phthalocyanine compound and the fatty acid with long alkyl chain in an organic solvent, (2) is the step of developing an organic solution on the water surface, (3) is the step of volatilizing the organic solvent, (4) is the step of accumulating a thin layer on a substrate and (5) is the step of baking the thin film.

Although the above described embodiment illustrated the phthalocyanine compound having Cu as a central metal, the present invention is not limited to this compound and the same effect as that in this embodiment can be attained by phthalocyanine compound having the central metal of Co, Ni, Fe, Al, Mg, Zn or Si.

Although stearic acid was used in the above described embodiment, any fatty acid, if it has a long chain alkyl group represented by a general formula $C_nH_{2n+1}COOH$, can be used. In addition, carboxylic acid having double bond or triple bond represented by general formulas such as $C_nH_{2n-1}COOH$, $C_nH_{2n-3}COOH$ and the like can be used other than one having the long chain alkyl group. In addition, carboxylic acid having a short branch at one portion of the long chain may be used.

For the above described saturated fatty acid and the above described unsaturated fatty acid, it is preferable to select the number of n such that their compound may be solid at an ordinary temperature and they can be removed by baking at an ordinary temperature or baking at a low pressure (under a low vacuum). If n is 8 selected in the range of 8 or more to 20 or less, it can be always preferably used.

EXAMPLE 2

A phthalocyanine compound having four carboxyl groups of an essential minimum size introduced thereto, shown in FIG. 6, was used as an organic semiconductor compound. Like the embodiment 1, a Pc compound and stearyl amine were mixed at a ratio of 1:4 in a mixture solvent of dimethylformamide, dimethylacetamide or N-methylpyrolidone and chloroform (such that its concentration may be $10^{-4}M$ by calculating with the Pc). Thereafter, it was developed on the water surface and accumulated on a glass substrate after the solvent was volatilized. Then, a thin film of the Pc compound was obtained by baking it for two hours at 320° C. and removing the amine. The removal of the amine was confirmed by the IR spectra by the same method as that of the embodiment 1.

The steps of forming the thin film in accordance with this embodiment were as follows:

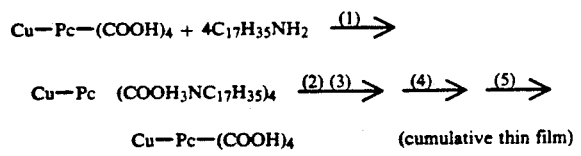

where the meaning of the steps of (1), (2), (3), (4) and (5) are the same as described above.

According to the above described embodiment, an organic semiconductor thin film having no insulating side chain and an excellent electric characteristic was also obtained.

EXAMPLE 3

In this example, the films described in the examples 1 and 2 were accumulated alternately. More specifically, a monomolecular layer having amino groups at side chains of the Pc ring and a monomolecular layer having carboxyl groups at side chains of the Pc ring were accumulated alternately. After the accumulation, amide bonding was formed at each layer by causing a condensation reaction by dehydration. In this example, since the condensation reaction by dehydration occurred between or within the layers, high molecular weight substances were generated, whereby thermally and mechanically stabilized film could be obtained. In addition, since its solvent resistance was improved, it was not dissolved in the developing solvent.

The steps of forming a thin film in accordance with this embodiment were as follows:

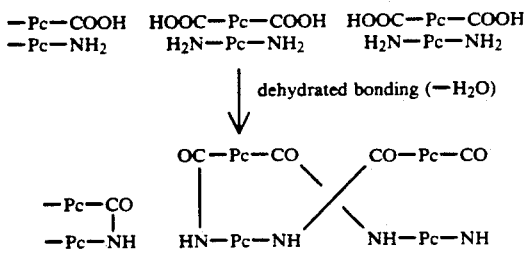

EXAMPLE 4

A Pc compound ($X=CONHC_nH_{2n+1}$, $NHCOC_nH_{2n+1}$) having long chain alkyl groups bonded to a side chain of a Pc ring by peptide bonding, which structure is shown in FIG. 1, was used as an organic semiconductor compound. The Pc compound was dissolved in a mixed solvent of dimethylacetamide and chloroform (concentration is $10^{-4}M$) and developed on pure water and then a thin film was accumulated on a glass substrate by a dipping method (substrate speed is 5 mm/min) after the solvent was volatilized. Thereafter, the alkyl chain portion of the long chain was removed by hydrolizing it under the existence of acid catalyst. As a result, there was formed a phthalocyanine thin film having a short side chain in which a phthalocyanine ring plane was oriented parallel to the substrate surface. The conditions of the hydrolysis were as follows. That is, after the thin layer was accumulated on the glass substrate and baked for one hour at 200° C., the whole substrate was refluxed for four hours in water solutions to which concentrated sulfuric acid was added by the amount of the solution. The confirmation of the removal of the hydrocarbon side chain by the hydrolysis was made by the IR.

The steps of forming the thin film in accordance with this example were arranged as follows:

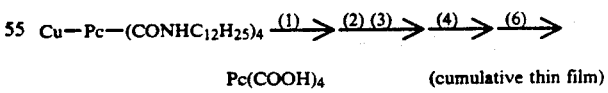

where the meaning of the steps of (1), (2), (3) and (4) is the same as described above and (6) is the step of hydrolyzing.

Although a description was made of a case in which the peptide bonding was hydrolized with the acid catalyst in this example, the alkyl chain portion of the long chain may be removed in plasma processing by $O_2$ plasma. More specifically, the alkyl chain portion of the long chain could be removed by the treatment for five minutes at output 200 W, $O_2$ gas flow 40 SCCM and at a substrate temperature 150° C. It is preferable to remove this alkyl chain portion each time one thin layer is accumulated. It was confirmed by IR absorption spectra that the absorption of 2800~3000 cm$^{-1}$ (CH stretching vibration) was lost.

In addition, although the Pc compound having the long chain alkyl groups bonded to the Pc ring by the peptide bonding was described in the above example, even if a Pc compound having long chain alkyl groups bonded to the Pc ring by an ester bonding as shown in FIG. 1 was used, the same film formation could be implemented.

In addition, although a description was made by illustrating various phthalocyanine compounds as organic semiconductor compounds in the above examples, 1, 2, 3 and 4, the present invention is not limited to these and the film can be formed by introducing the long chain hydrocarbon groups by the same method even when porphyrin compound, cyanin color compound, triphenylmethane compound or spiropyrane compound is used.

EXAMPLE 5

Figure 7:
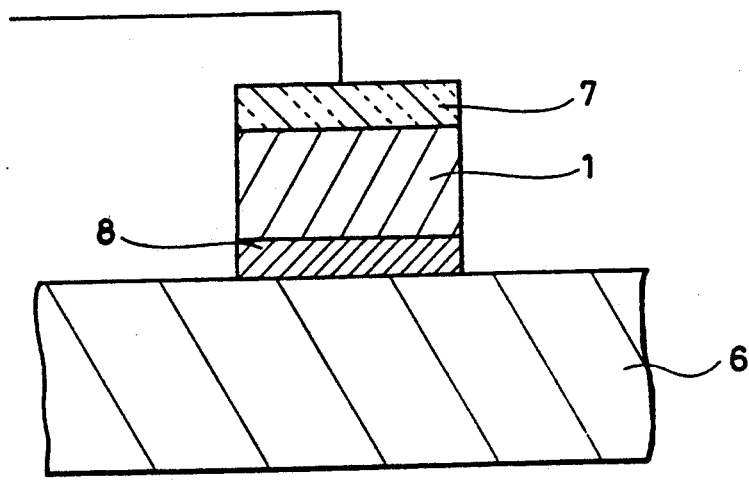
FIG. 7 is a sectional view of a photoelectric transfer device in accordance with the present invention.

FIG. 7 is a sectional view of an photoelectric transfer device using an organic semiconductor thin film formed by a method in accordance with the present invention.

Referring to FIG. 7, a lower electrode 8 is formed on a substrate 6, an organic semiconductor thin film 1 is formed on the lower electrode 8 and an upper electrode 7 was formed on the organic semiconductor thin film 1. The substrate 6 is formed of a transparent substance such as glass, quartz or the like. When an optically opaque substance is used as the substrate 6, the upper electrode 7 is preferably a transparent electrode such as ITO and the like.

When light was radiated, electrons and electron holes were formed in the organic semiconductor thin film 1 by light excitation. Since these electrons and electron holes served as carriers, the lower electrode 8 and the upper electrode 7 were rendered to be conductive, so that a current flowed between both electrodes.

A description is made of a method for manufacturing the photoelectric transfer device shown in FIG. 7.

FIGS. 8A to 8E show steps of manufacturing the photoelectric transfer device shown in FIG. 7.

Figure 8B:
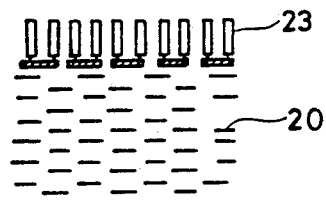
FIGS. 8A to 8E show a method for forming the photoelectric transfer device shown in FIG. 7.
Figure 8A:
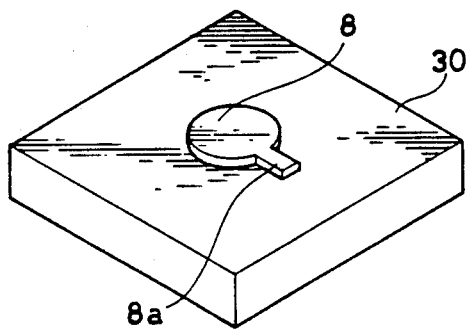

Referring to FIG. 8A, a thin film of gold is formed to the thickness of 1000 Å by vacuum vaporization as lower electrode 8 on a glass plate 30 (20×50 mm). The lower electrode 8 is formed to be circular having at a portion thereof a projection 8a to provide a contact with the outside. Thereafter, an organic semiconductor thin film is formed on the lower electrode 8 by using the method shown in the embodiment 1.

Figure 8C:
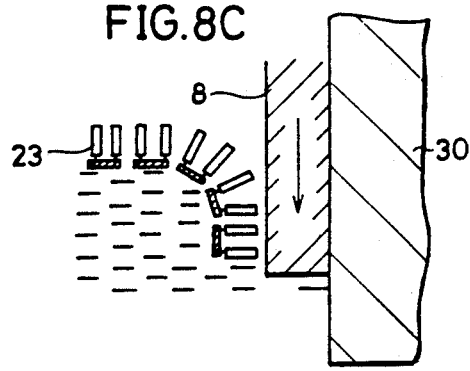

More specifically, a phthalocyanine compound including the amino group and stearic acid which is a fatty acid with long alkyl chain generally represented by $C_nH_{2n+1}COOH$ are mixed in the ratio of 1:4 to provide a combination (hereinafter referred to as an amine salt). The amine salt is dissolved in an appropriate organic solvent such as chloroform, xylene, dimethylacetamid, N-methylpyrolidone such that the concentration of the Pc compound becomes approximately $1.0 \times 10^{-4}$M. The resulting organic solution is dripped in water 20, as shown in FIG. 8B. The organic solution is spread over the surface of the water 20. Thereafter, the organic solvent is volatilized, leaving the monomolecular film 23 of the amine salt on the surface of the water 20. Referring to FIG. 8C, a glass plate 30 including an lower electrode 8 is lowered to be dipped in the water 20. Then, the monomolecular film 23 of the amine salt is attached to the lower electrode 8. The lifting speed of the substrate 21 in the dipping method is 5 mm/min.

Figure 8E:
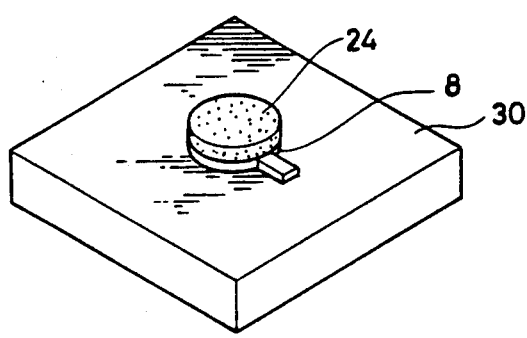
Figure 8D:
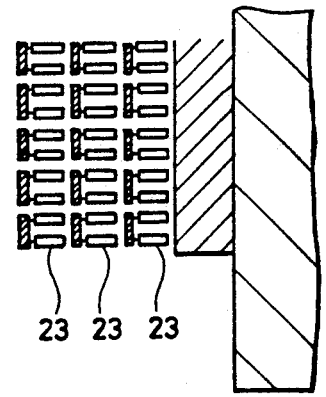

Referring to FIG. 8D, several to several ten layers of the monomolecular films 23 are accumulated on the substrate by repeating the same operation. During the operation, the thin film 24 may be formed on portions other than the lower electrode 8. In that case, patterning is carried out so that the thin film 24 is provided only on the lower electrode 8. Referring to FIG. 8E, the thin film 24 is formed on the lower electrode 8.

Thereafter, the stearic acid is volatilized and removed by heat treatment in $N_2$ for 1 to 2 hours at 300° to 320° C.

Finally, indium thin oxide (ITO) is formed by sputtering on the thin film 24 to form an upper electrode 7, whereby the photoelectric transfer device shown in FIG. 7 is provided.

By way of comparison, the LB film was formed in a similar manner using tetra-tert-butyl phthalocyanine copper (10-layer laminate) and the photoelectric transfer device having the same structure was formed. Then, photoconductivity was measured using the above described device. Current changes, when the sample was irradiated with light from xenon lamp through a filter of 620 nm, were measured on both samples with a voltage held constant (10 V). As a result, the photoelectric transfer device using the LB film of the present invention showed an excellent ratio of amplification (irradiating time/dark time) of $10^3$ as compared with that of 5~10 of the photoelectric transfer device using the conventional tetra-tert-butyl phthalocyanine copper. The reason of this excellent ratio of amplification is that the organic semiconductor thin film in accordance with the present invention was of a laminated cumulative film having the Pc ring was oriented parallel to the substrate. In addition, it was found that the rise of the amplification ratio was more increased by doping iodine and the like.

Figure 9:
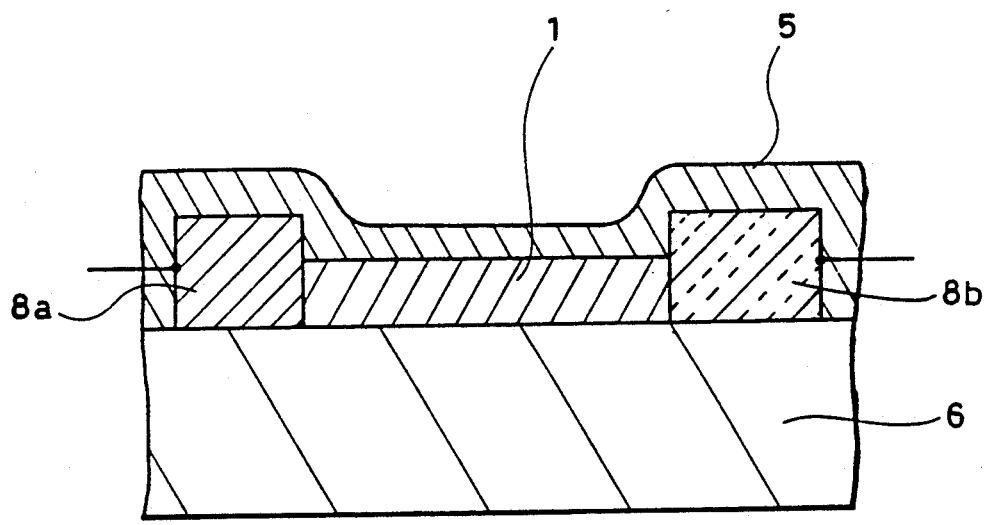
FIG. 9 is a sectional view of a photoelectric transfer device in accordance with another embodiment of the present invention.

FIG. 9 is a sectional view of another embodiment in which the organic semiconductor thin film in accordance with the present invention was applied to the photoelectric transfer device. One electrode 8a and the other electrode 8b are formed on a substrate 6. An organic semiconductor thin film 1 is formed on the substrate 6 so as to be sandwiched by the one electrode 8a and the other electrode 8b. A protective film 5 is formed so as to cover these. Either the protective film 5 or the substrate 6 or both of them are preferably formed of a transparent substance in this structure. The thus structured photoelectric transfer device showed the excellent ratio of amplification.

EXAMPLE 6

Figure 10:
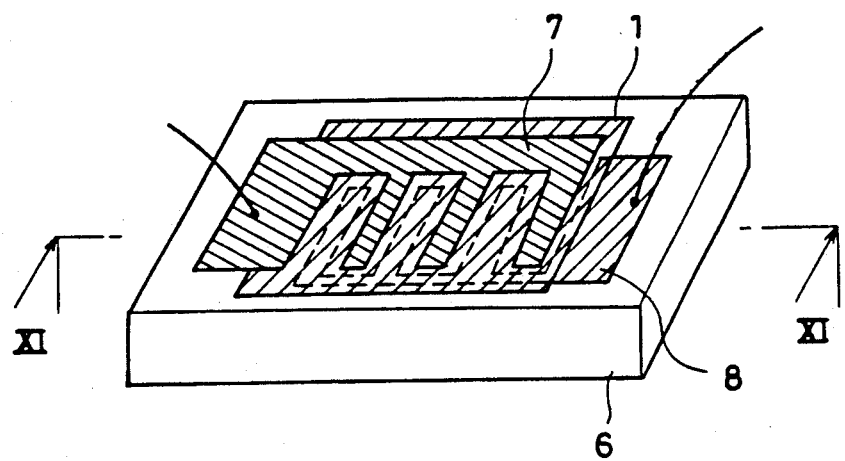
FIG. 10 is a schematic view of a gas sensor in accordance with the present invention.
Figure 11:
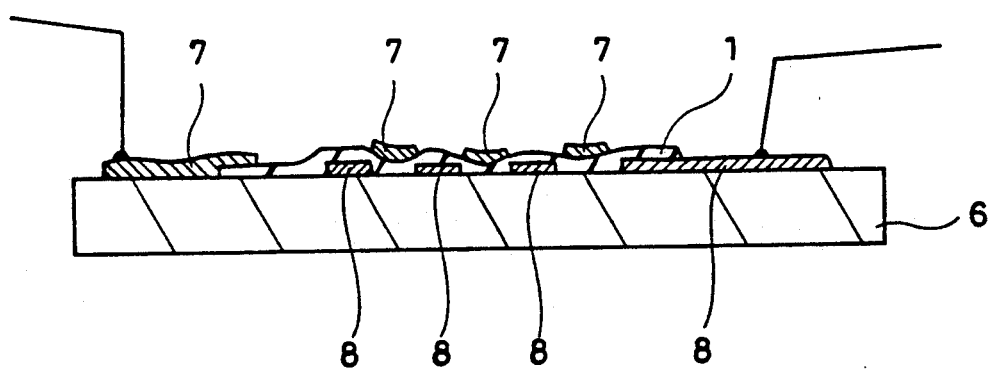
FIG. 11 is a sectional view taken along a line XI—XI in FIG. 10.

FIG. 10 is a perspective view of a gas sensor using the organic semiconductor thin film formed in accordance with the method of the present invention. FIG. 11 is a sectional view taken along a line XI—XI in FIG. 10. Referring to these figures, a comb-shape lower electrode 8 is formed on a substrate 6 (glass substrate), an organic semiconductor thin film 1 is formed on the lower electrode 8 and then a comb-shape upper electrode 7 is formed thereon.

When the thus structured sensor portion was exposed to $NO_2$ gas, for example, the conductivity of the organic semiconductor thin film 1 changed due to the absorption of the gas. The gas could be detected by representing the change of the conductivity by a current value and comparing it with the current value of a comparison sensor portion.

Next, a description is made of the steps of manufacturing this gas sensor.

First, gold is formed to be comb-shaped with 1000 Å in thickness on a glass substrate 6 which was washed enough, as a lower electrode 8 by vacuum deposition. The comb shape is formed by repeating a gold pattern with a width of 1 mm and a space portion with a width of 3 mm.

Then, the Pc compound is accumulated by 20 layers on the substrate 6 in accordance with the method of the example 1, so that the organic semiconductor thin film 1 is formed. Then, as the upper electrode 7, gold is formed to be comb-shaped by vapored position with 1000 Å in thickness.

Figure 3:
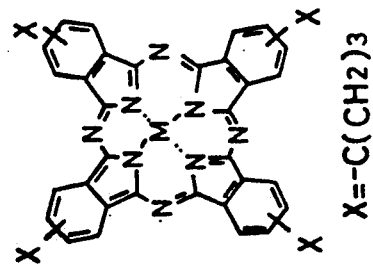
FIG. 3 shows structural formulas of an another phthalocyanine compound.
Figure 4A:
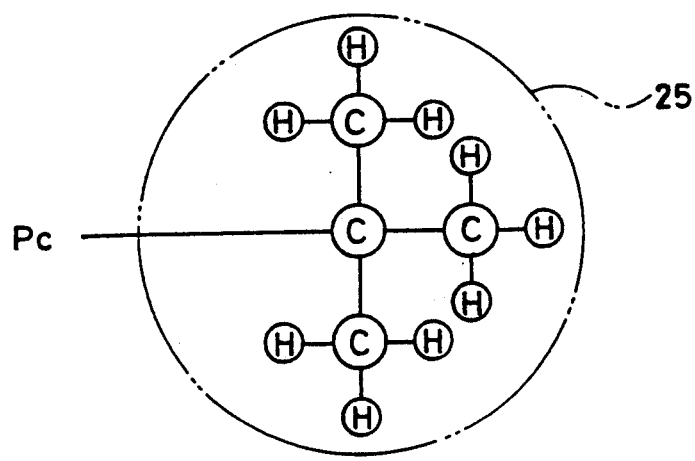
FIGS. 4A to 4C are schematic diagrams showing volumes of various substituent groups coupled to the phthalocyanine compound.
Figure 4B:
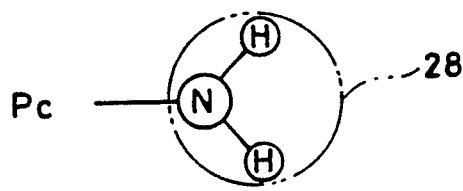
Figure 4C:
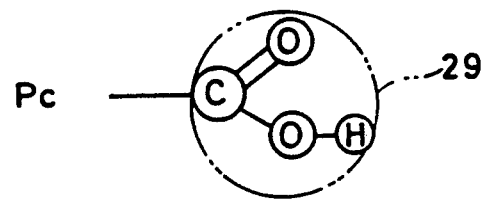
Figure 5A:
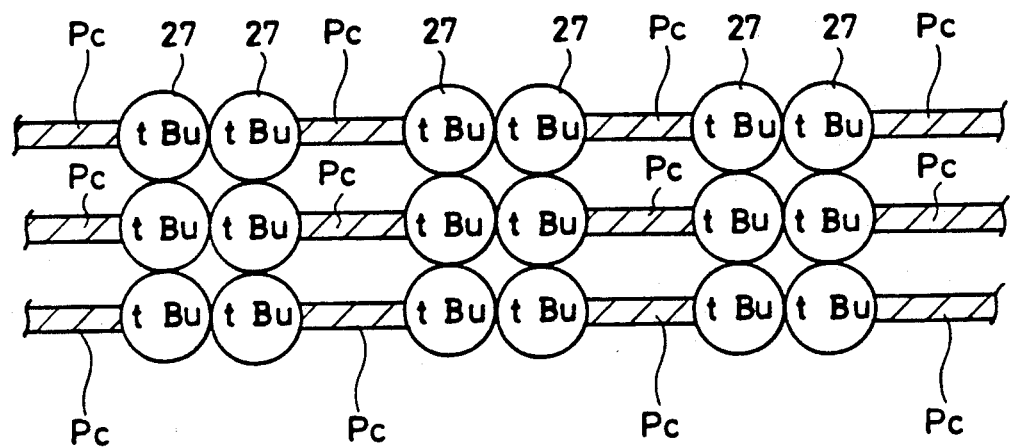
FIG. 5A schematically shows a cross section of an organic semiconductor thin film formed by using a phthalocyanine compound having t-butyl group, while FIG. 5B schematically shows a cross section of an organic semiconductor thin film of the present invention.
Figure 5B:
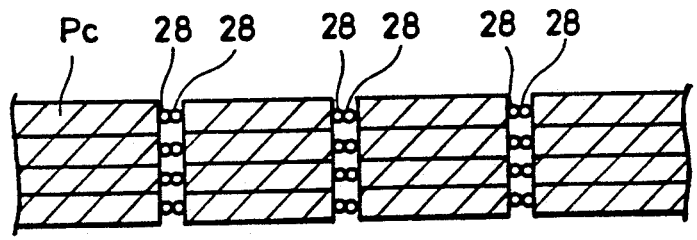

By way of comparison, a gas sensor was formed under the same conditions as those in this embodiment using the Pc compound having substituent groups in asymmetrical positions as shown in FIG. 3 and its performance was compared with that of the above described gas sensor. When the sensor of the present invention was exposed to $NO_2$ gas atmosphere (100 ppm), approximately double current was detected as compared with the conventional sensor (which was made using the Pc compound shown in FIG. 3). This device could be used repeatedly by removing an absorbed gas by baking.

In addition, when a gas sensor was formed using the organic semiconductor thin film made by the method in the embodiment 3, it was found that a film quality was stabilized because of interlayer bonding, so that the durability thereof was improved.

Figure 12:
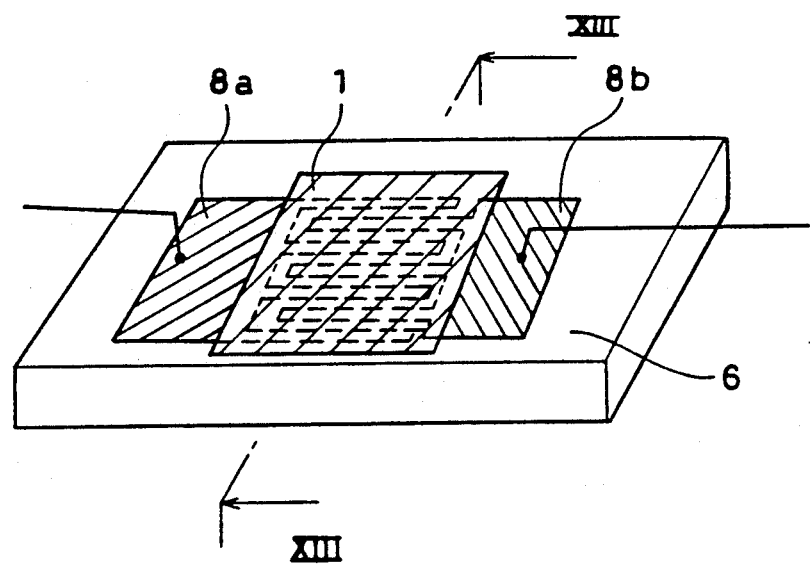
FIG. 12 is a perspective view of a gas sensor in accordance with another embodiment of the present invention.
Figure 13:
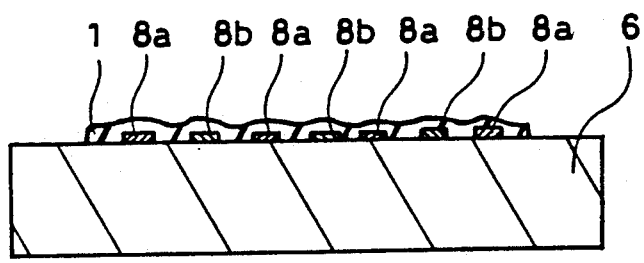
FIG. 13 is a sectional view taken along a line XIII—XIII in FIG. 12.

FIG. 12 is a perspective view of another example in which the organic semiconductor thin film in accordance with the present invention is applied to a gas sensor. FIG. 13 is a sectional view taken along a line XIII—XIII in FIG. 12. Referring to these figures, one electrode 8a of a comb shape is formed on a substrate (glass substrate) 6, the other comb-shaped electrode 8b is formed so as to be engaged in the comb-shaped electrode 8a and then an organic semiconductor thin film 1 is formed on these electrodes.

Next, a description is made of the steps of manufacturing this gas sensor. Referring to FIGS. 6 and 7, one comb-shaped electrode 8a of a gold electrode and the other comb-shaped electrode 8b are formed to be 1000 Å in thickness so as to be engaged with each other on the glass substrate 6 by vapor deposition. The LB film is accumulated by 25 layers thereon in accordance with the method of the example 2.

A $NH_3$ gas was detected using the thus formed gas sensor and that gas sensor was compared with a gas sensor having the LB film formed of tetra-cumyl phenoxyphthalocyanine which was the example in the past. The ratio of response current $I/I_0$ (I: a response current value of the gas sensor in accordance with this example and $I_0$: a response current value of the gas sensor using tetra-cumyl phenoxyphthalocyanine) in the $NH_3$ gas of 2 ppm (volume ratio) was 3-3.5, and it was found that the sensitivity of the gas sensor in accordance with this example was raised three times as much as the one in the past.

EXAMPLE 7

Figure 14:
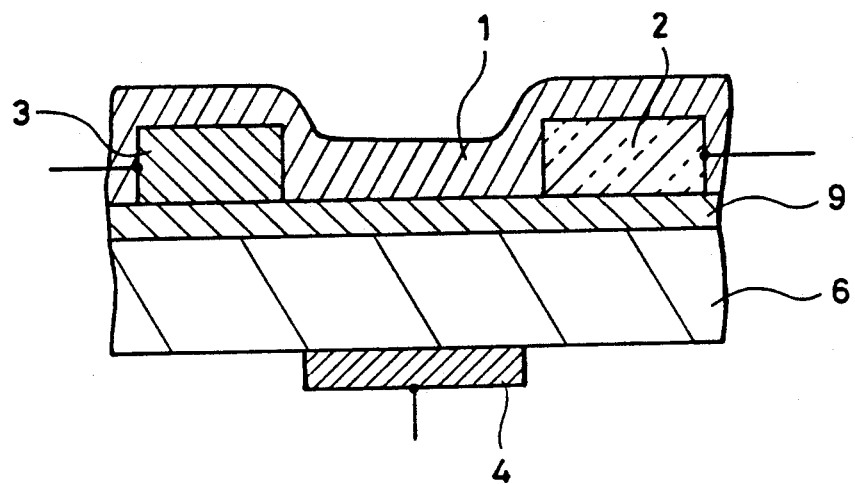
FIG. 14 is a sectional view of an organic semiconductor transistor in accordance with the present invention.

FIG. 14 is a sectional view of a transistor having the organic semiconductor thin film made by the method in accordance with the present invention.

Referring to FIG. 14, an insulating film 9 is formed on one surface of a substrate 6 (for example silicon substrate) and a source electrode 2 and a drain electrode 3 are formed on the insulating film 9. An organic semiconductor thin film 1 is formed on the substrate 6 so as to cover the source electrode 2 and the drain electrode 3. A gate electrode 4 is formed on the other surface of the substrate 6.

When a negative voltage ($-10$ V) was applied to the gate electrode of such FET type organic thin film transistor, a current flowed between the source and drain, which showed a switching characteristic. In case of a voltage 0 V, very little current flowed.

Next, a description is made of the steps of forming this organic thin film transistor. Referring to FIG. 8, an n type silicon substrate (resistivity $4 \sim 16$ Ωcm) serving as the substrate 6 is prepared and formed to be 0.3 mm in thickness by polishing. A gate electrode 4 is formed by depositing Al by vapor deposition on the other surface of the substrate 6. A $SiO_2$ film serving as an insulating film 9 is formed to be 0.5 μm in thickness on one surface of the substrate 6 by thermal oxidation or sputtering method. Then, gold is formed to be 1000 Å in thickness on the insulating film 9 by vapor deposition as source and drain electrodes 2 and 3. Finally, the LB film is accumulated by 50 layers on the substrate by the method shown in the example 1. In this way, the organic thin film transistor shown in FIG. 8 is formed.

Figure 15:
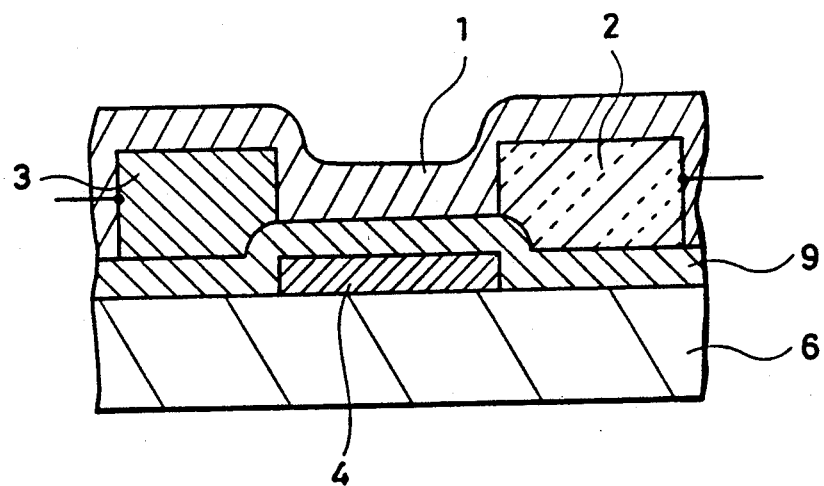
FIG. 15 is a sectional view of an organic semiconductor transistor in accordance with another embodiment of the present invention.

FIG. 15 is a sectional view of another embodiment of the transistor having the organic semiconductor thin film made by the method in accordance with the present invention.

Referring to FIG. 15, a gate electrode 4 of a gold electrode is formed on a substrate 6 (for example, glass substrate). An insulating film 9 is formed on the whole surface of the substrate 6 comprising the gate electrode 4. A source electrode 3 and a drain electrode 2 are formed on the insulating film 9 and an organic semiconductor thin film 1 is formed on the whole surface so as to cover these source and drain electrodes 2 and 3.

Next, a description is made of a method for manufacturing this organic thin film transistor.

A gold electrode was formed to be 1000 Å in thickness on the glass substrate 6 as the gate electrode 4 by vapor deposition. Then, a poly-imide precursor was spincoated as an insulating layer thereon and baked for one hour at 300° C., and finally a poly-imide layer of 0.5 μm in thickness serving as the insulating film 9 was formed. Then, gold electrodes (source and drain electrodes 2 and 3) were formed thereon by vapor deposition. The gold electrodes were 1000 Å in thickness. Finally, the LB film serving as the organic semiconductor thin film 1 was accumulated by 45 layers on the whole surface of the substrate 6 by the manufacturing method shown in the example 1.

In the thus formed organic thin film transistor, current flow did not occur between source and drain when the gate voltage was 0 V, but when the gate voltage became $-12$ V, a current flowed between source and drain which showed switching characteristic.

Figure 16:
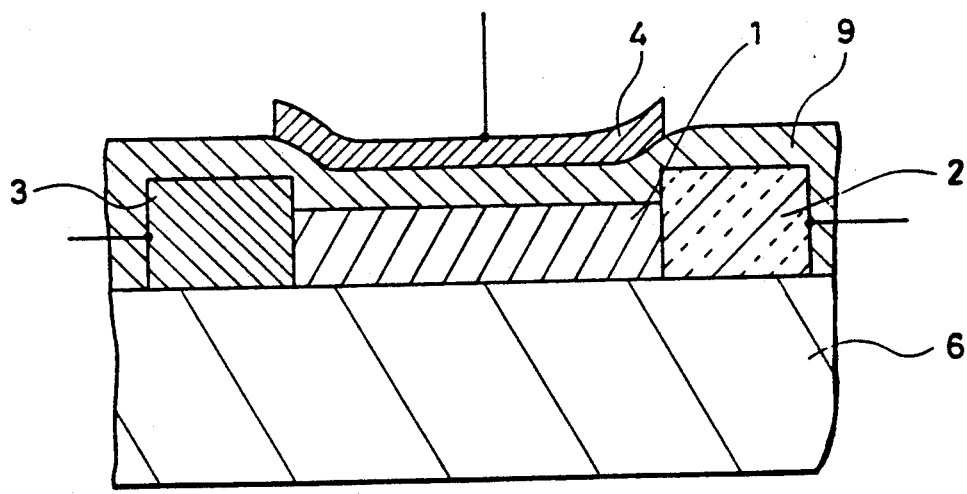
FIG. 16 is a sectional view of an organic semiconductor transistor in accordance with a further embodiment of the present invention.

FIG. 16 is a sectional view of a further embodiment of the transistor having the organic semiconductor thin film made by the method in accordance with the present invention.

Referring to FIG. 16, source and drain electrodes 2 and 3 are formed on a substrate 6, an organic semiconductor thin film 1 is formed so as to be sandwiched by the source and drain electrodes 2 and 3 and then an insulating film 9 is formed so as to cover these. A gate electrode 4 is formed on the insulating film 9.

A description is made of the steps of manufacturing the organic thin film transistor in accordance with this example.

Referring to FIG. 16, the source and drain electrodes 2 and 3 were formed to be 1000 Å in thickness by vapor deposition of gold. A LB film serving as the organic semiconductor thin film 1 was accumulated by 60 layers so as to be sandwiched by these source and drain electrodes 2 and 3 by the method described in the example 1. Then, a poly-imide precursor was applied by 0.5 μm in thickness by spincoating and finally baked for one hour at 250° C. to finish imidation and then the insulating film 9 was formed. Thereafter, a gold gate electrode 4 was formed to be 1000 Å in thickness on the insulating film 9 by vapor deposition.

In the thus formed organic thin film transistor, a current flow between source and drain hardly occurred when the gate voltage 0 V, but a current flowed between source and drain when the gate voltage was −12 V, which showed the switching characteristic.

According to the semiconductor device shown in the examples 5 to 7, since a silicon wafer and the like in having circuits formed thereon can be used as a substrate, a gas sensor, photoelectric transfer film, transistor and the like can be further formed on that substrate and, as a result, a device of a three dimensional structure can be easily obtained.

According to the manufacturing method of the organic semiconductor thin film in accordance with the present invention, an organic semiconductor compound is bonded to a long chain hydrocarbon and dissolved in an organic solvent and then a thin film is deposited on the substrate by a LB method from the organic solution in which the organic semiconductor compound and the long chain hydrocarbon are dissolved and finally the long chain hydrocarbon portion is removed from this thin film. Therefore, sufficiently dense packing and stacking is implemented between intermoleculars because bulky substituent group element does not remain on the thin film of the substrate. As a result, the organic semiconductor thin film having an improved characteristic as a semiconductor can be provided. When the organic semiconductor thin film formed in this manner is used in a semiconductor device, the performance of the semiconductor device is extremely improved. Furthermore, according to the method of the present invention, since a silicon wafer and the like having circuits formed thereon can be used, there is provided an effect that a gas sensor, a photoelectric transfer film, a transistor and the like can be further formed on that substrate and, subsequently, a device of a three dimensional structure can be easily formed.

The above described embodiments are only illustration in all respects and is not to be taken by way of limitation. The scope of the present invention is limited only by the terms of the appended claims not by the specification thereof. Various changes and modifications belonging to the equivalent scope of the claim are all within the scope of the present invention.

What is claimed is:

1. A semiconductor device comprising an organic semiconductor thin film formed by a method including the steps of:
    preparing an organic semiconductor compound including an amino group;
    preparing a long chain hydrocarbon including a carboxyl group which can be bonded to said amino group;
    bonding said organic semiconductor compound including said amino group to said long chain hydrocarbon including said carboxyl group for making said semiconductor compound to be dissolved in an organic solvent;
    making an organic solution by dissolving said organic semiconductor compound combined with said long chain hydrocarbon in said organic solvent;
    dropping said organic solution in an appropriate liquid for forming a layer of said organic solution on the surface of said liquid;
    removing said organic solvent from said layer of said organic solution for forming a layer of the combination of said organic semiconductor compound and said long chain hydrocarbon on the surface of the liquid;
    depositing said layer of the combination of said organic semiconductor compound and said long chain hydrocarbon on the surface of a substrate; and
    removing said long chain hydrocarbon from the layer of said combination for forming an organic semiconductor thin film consisting of said organic semiconductor compound including the amino group on the surface of said substrate.

2. A semiconductor device in accordance with claim 1 having a photoelectric transfer function.

3. A semiconductor device in accordance with claim 1 having the function of detecting a gas.

4. A semiconductor device in accordance with claim 1 having a switching function.

5. A semiconductor device comprising a semiconductor thin film formed by a method including the steps of:
    preparing an organic semiconductor compound having a carboxyl group;
    preparing a long chain hydrocarbon compound having an amino group which can be bonded to said carboxyl group;
    bonding said long chain hydrocarbon compound having said amino group to said organic semiconductor compound having said carboxyl group for making said organic semiconductor compound to be dissolved in an organic solvent;
    making an organic solution by dissolving said organic semiconductor compound combined with said long chain hydrocarbon in said organic solvent;
    dropping said organic solution in an appropriate liquid for forming a layer of the organic solution on the surface of the liquid;
    removing said organic solvent from said layer of said organic solution for forming a layer of the combination of said organic semiconductor compound and said long chain hydrocarbon on the surface of said liquid;
    depositing said layer of the combination of said organic semiconductor compound and said long chain hydrocarbon on a substrate; and
    removing said long chain hydrocarbon from said layer of said combination for forming an organic semiconductor film consisting of said organic semiconductor compound including the carboxyl group on the surface of said substrate.

6. A semiconductor device comprising a semiconductor thin film formed by a method including the steps of:
    preparing an organic semiconductor compound including a carboxyl group;
    preparing a long chain hydrocarbon compound having a hydroxyl group which can be bonded to said carboxyl group by a dehydration reaction;
    bonding said organic semiconductor compound to said long chain hydrocarbon compound by esterification, for making said organic semiconductor compound to be dissolved in an organic solvent;
    making an organic solution by dissolving the ester of said long chain hydrocarbon compound and said organic semiconductor compound in said organic solvent;
    dropping said organic solution in an appropriate liquid for forming a layer of said organic solution on the surface of the liquid;
    removing said organic solvent from said organic solution for forming a layer of the ester of said organic semiconductor compound and said long chain hydrocarbon on the surface of said liquid;
    depositing the layer of the ester of said organic semiconductor compound and said long chain hydrocarbon compound on a substrate; and
    removing said long chain hydrocarbon from the layer of said ester for forming an organic semiconductor thin film consisting of said organic semiconductor compound including said carboxyl group on said substrate.

7. A semiconductor device comprising an organic semiconductor thin film formed of an organic semiconductor compound selected from the group consisting of a phthalocyanine compound having an amino group, a porphyrin compound having an amino group, a cyanine dye compound having an amino group, a triphenylmethane compound having an amino group, a spiropyran compound having an amino group; a phthalocyanine compound having a carboxyl group, a porphyrin compound having a carboxyl group, a cyanine dye compound having a carboxyl group, a triphenylmethane compound having a carboxyl group and a spiropyran compound having a carboxyl group.

* * * * *